(12) United States Patent
Fell

(10) Patent No.: US 8,828,080 B2
(45) Date of Patent: Sep. 9, 2014

(54) METHOD AND SYSTEM FOR KNEE JOINT REPAIR

(76) Inventor: Barry M. Fell, Hummelstown, PA (US)

( * ) Notice: Subject to any disclaimer, the term of this patent is extended or adjusted under 35 U.S.C. 154(b) by 1024 days.

(21) Appl. No.: 11/361,878

(22) Filed: Feb. 21, 2006

(65) Prior Publication Data

US 2006/0190078 A1    Aug. 24, 2006

Related U.S. Application Data

(60) Provisional application No. 60/655,050, filed on Feb. 22, 2005.

(51) Int. Cl.
*A61F 2/30* (2006.01)
*A61F 2/38* (2006.01)
*A61F 2/46* (2006.01)
*A61B 17/88* (2006.01)

(52) U.S. Cl.
CPC ... *A61F 2/30756* (2013.01); *A61F 2002/30062* (2013.01); *A61F 2002/4685* (2013.01); *A61F 2002/467* (2013.01); *A61F 2/4618* (2013.01); *A61F 2250/0068* (2013.01); *A61F 2002/30581* (2013.01); *A61F 2/3872* (2013.01); *A61F 2/38* (2013.01); *A61F 2002/3009* (2013.01); *A61F 2002/3068* (2013.01); *A61F 2002/30948* (2013.01); *A61F 2002/30754* (2013.01); *A61B 17/8808* (2013.01); *A61F 2002/4658* (2013.01); *A61F 2250/0091* (2013.01); *A61F 2210/0004* (2013.01); *A61F 2/30942* (2013.01); *A61F 2310/00011* (2013.01); *A61F 2002/30971* (2013.01); *A61F 2310/00179* (2013.01)
USPC ...................................... 623/14.12

(58) Field of Classification Search
CPC .................... A61B 17/3472; A61F 2/3872
USPC ............ 606/92, 93, 94, 95, 86, 99, 100, 105;
623/14.12, 20.14, 20.16, 20.32, 20.33,
623/23.5, 23.61, 902, 908, 909, 911
See application file for complete search history.

(56) References Cited

U.S. PATENT DOCUMENTS

| 4,399,814 | A | * | 8/1983 | Pratt et al. ........................ 606/94 |
| 4,488,549 | A | * | 12/1984 | Lee et al. ........................ 606/94 |
| 4,595,006 | A | * | 6/1986 | Burke et al. ..................... 606/94 |
| 5,123,927 | A | | 6/1992 | Duncan et al. |
| 5,176,683 | A | * | 1/1993 | Kimsey et al. .................. 606/86 |
| 5,480,450 | A | * | 1/1996 | James et al. ................. 623/23.2 |
| 5,556,429 | A | | 9/1996 | Felt |

(Continued)

FOREIGN PATENT DOCUMENTS

| WO | 0217821 | 3/2002 |
| WO | 2004049981 | 6/2004 |
| WO | 2004078134 | 9/2004 |

OTHER PUBLICATIONS

Extended European Search Report for EP06735772, dated Apr. 26, 2010.

*Primary Examiner* — Brian Pellegrino
(74) *Attorney, Agent, or Firm* — Brooks Kushman P.C.

(57) ABSTRACT

A method and system for repairing a defect area in a surface of a joint include providing a mold having a first surface and a second surface, positioning the mold within the joint such that at least part of the mold first surface overlies the defect area, and depositing a repair material under the mold first surface within the defect area to create a repaired site within the joint.

16 Claims, 6 Drawing Sheets

(56) References Cited

U.S. PATENT DOCUMENTS

| | | |
|---|---|---|
| 5,693,099 A * | 12/1997 | Harle .................... 623/23.19 |
| 5,735,903 A | 4/1998 | Li et al. |
| 5,795,353 A | 8/1998 | Felt |
| 5,800,439 A * | 9/1998 | Clyburn .................... 606/94 |
| 6,110,211 A | 8/2000 | Weiss |
| 6,140,452 A | 10/2000 | Felt et al. |
| 6,306,177 B1 * | 10/2001 | Felt et al. .................... 623/23.6 |
| 6,352,558 B1 | 3/2002 | Spector |
| 6,355,067 B1 * | 3/2002 | Bloebaum .................... 623/16.11 |
| 6,443,988 B2 | 9/2002 | Felt et al. |
| 6,652,587 B2 | 11/2003 | Felt et al. |
| 6,942,475 B2 | 9/2005 | Ensign et al. |
| 2003/0055502 A1 | 3/2003 | Lang et al. |
| 2003/0216669 A1 | 11/2003 | Lang et al. |
| 2004/0107000 A1 | 6/2004 | Felt et al. |
| 2004/0204760 A1 | 10/2004 | Fitz et al. |
| 2004/0236424 A1 | 11/2004 | Berez et al. |
| 2004/0247641 A1 | 12/2004 | Felt et al. |
| 2006/0015117 A1 | 1/2006 | Haines |
| 2006/0030944 A1 | 2/2006 | Haines |
| 2006/0058882 A1 | 3/2006 | Haines |
| 2006/0095138 A1 | 5/2006 | Truckai et al. |
| 2007/0198022 A1 * | 8/2007 | Lang et al. .................... 606/88 |

* cited by examiner

METHOD AND SYSTEM FOR KNEE JOINT REPAIR

CROSS-REFERENCE TO RELATED APPLICATIONS

This application claims the benefit of U.S. provisional application Ser. No. 60/655,050 filed Feb. 22, 2005.

BACKGROUND OF THE INVENTION

1. Field of the Invention

The present invention relates to a method and system for restoration and repair of a body joint, such as the knee.

2. Background Art

Articular cartilage and meniscal cartilage provide the mobile weight bearing surfaces of the knee joint. Damage to these surfaces is generally due to genetic predisposition, trauma, and/or aging. The result is usually the development of chondromalacia, thinning and softening of the articular cartilage, and degenerative tearing of the meniscal cartilage. Various methods of treatment are available to treat these disease processes. Each option usually has specific indications and is accompanied by a list of benefits and deficiencies that may be compared to other options.

Especially in the case of early onset osteoarthritis, the destruction of the articular material is generally localized to specific areas on the femoral condyle and tibial plateau. It is rarely widespread and often lacking the presence of eburnated bone. As the disease progresses, the damage to the articular material increases and patches of exposed bone may appear, with the area of degeneration typically being irregularly shaped and of varying depth. At this stage, it is often common to see the formation of osteophytes along the periphery of the tibial plateau and femoral condyle in response to the increased localized loading due to the disease changing the shape of the articulating members (FIGS. 1a and 1b).

The healthy knee joint has a balanced amount of joint cartilage across the four surfaces of this bicompartmental joint (medial femoral condyle, medial tibial plateau, lateral femoral condyle, and lateral tibial plateau). In patients with osteoarthritis, the degenerative process typically leads to an asymmetric wear pattern that leaves one compartment with significantly less articular cartilage covering the distal portions (or weight bearing area) of the tibia and femur than the other compartment. Most commonly, the medial compartment of the knee joint is affected more than the lateral compartment.

As the disease progresses, large amounts of articular cartilage are worn away. Due to the asymmetric nature of the erosion, the alignment of the mechanical axis of rotation of the femur relative to the tibia becomes tilted down towards the compartment which is suffering the majority of the erosion. The result is a varus (bow-legged) deformity in the case of a medial compartment disease predominance, or a valgus (knock-kneed) deformity in the case of lateral compartment disease predominance. Factors such as excessive body weight, previous traumatic injury, knee instability, the absence of the meniscus, and genetic predisposition all affect the rate of the disease.

Osteoarthritis is usually defined in stages of Grade I through V, with Grade III revealing significant articular cartilage loss, Grade IV revealing some eburnation of the subchondral bone, and Grade V detailing both significant articular loss and bone loss. The disease manifests itself as periodic to continuous pain that can be quite uncomfortable for the patient. The cause of this pain is subject to many opinions but it is apparent that, as the joint compartment collapses, the collateral ligament on the side of the predominant disease becomes increasingly slack (like one side of a pair of loose suspenders), and the tibial and femoral axes move, for example, from a varus to a valgus condition. This increases the stress on the opposing collateral ligament as well as the cruciate ligaments, and shifts the load bearing function of this bicompartmental joint increasingly towards the diseased side. This increasing joint laxity is suspected of causing some of the pain one feels. In addition, as the bearing loads are shifted, the body responds to the increased loading on the diseased compartment with an increased production of bony surface area (osteophytes) in an attempt to reduce the ever-increasing area unit loading. All of this shifting of the knee component geometry causes a misalignment of the mechanical axis of the joint. This misalignment causes an increase in the rate of degenerative change to the diseased joint surfaces, causing an ever-increasing amount of cartilage debris to build up in the joint, and further causing joint inflammation and subsequent pain.

Currently, there is a void in options used to treat the relatively young patient with moderate to severe chondromalacia involving mainly one compartment of the knee. Current treatments include NSAIDS, cortisone injections, hyaluronic acid (HA) injections, and arthroscopic debridement. Some patients cannot tolerate or do not want the risk of potential side effects of NSAIDS. Repeated cortisone injections actually weaken articular cartilage after a long period of time. HA has shown promising results, but is only a short term solution for pain. Arthroscopic debridement alone frequently does not provide long lasting relief of symptoms.

Unfortunately, the lack of long term success of these treatments leads to more invasive treatment methods. Osteochondral allografts and microfracture techniques are indicated for small cartilage defects that are typically the result of trauma. These procedures are not suitable for addressing large areas of degeneration. In addition, osteochondral allografts can only be used to address defects on the femoral condyle, as tibial degeneration cannot be addressed with this technique. High tibial osteotomy (HTO) corrects the varus malalignment between the tibia and the femur but, because it is performed below the joint line, it does not fill the cartilage void or re-tension the medial collateral ligament (MCL). Removing bone and changing the joint line complicates the conversion to total knee arthroscopy (TKA). In addition, an HTO does leave a hard sclerotic region of bone which is difficult to penetrate, making conversion to a total knee replacement (TKR) technically challenging.

Currently, patients with large joint defects require replacement of the existing surfaces with materials other than articular cartilage. This is only possible with a primary (first arthroplasty performed on the joint) total (TKR) or uni-condylar (UKR) knee replacement. These procedures require the resection of significant amounts of the underlying bone structure; typically 7-9 mm. Primary procedures have typical functional life spans of 5-15 years, and thus younger patients undergoing this procedure will likely require revision (secondary) surgery as they age. However, the amount of bone loss that is inherent in these procedures makes a revision procedure much more difficult in the future as even more bone must be removed. Revision total knee replacement surgery is usually extensive and results in predictably diminished mechanical life expectancy. Therefore, it is best to delay this type of bone resecting surgery as long as possible.

Treatments such as osteochondral transplants (OATS procedure) fill defects with a series of small transplanted plugs of bone and cartilage. Metallic plugs, such as those described in U.S. Pat. Nos. 6,520,964 and 6,610,067, have also been used in an attempt to repair smaller defects in the tibial or femoral surfaces. Larger defects, such as avascular necrosis (AVN) are typically treated with donor (cadaver) allografts. Both methods have achieved limited success, as neither method is able to completely transition from the repaired defect area to the surrounding healthy areas without the creation of localized areas of high stress concentration, leading to premature failure.

Mobile prostheses may be implanted to attempt to restore joint function in the osteoarthritic patient. Such prostheses are typically designed to move over a relatively flat, smooth joint surface during the patient ROM. However, in the typical, moderately diseased osteoarthritic patient, the subchondral bone of both the plateau and condyle have become somewhat remodeled and reshaped due to the eccentric loading of the medial compartment. Once the prosthesis is implanted, there may be further "reshaping" of these bearing surfaces as well as the underlying bony structure until their geometries are conformal with the prosthesis shape, thereby possibly leading to pain. Once the joint is realigned to a neutral or valgus condition, the soft tissue, which has tolerated the varus alignment for so many years, may be painfully stressed into this new alignment. Only under-correction of the alignment would prevent this occurrence, but this option would leave joint instability for the patient.

BRIEF DESCRIPTION OF THE DRAWINGS

FIG. 11a is a schematic illustration of the mold depicting vacuum and fill ports and FIG. 11b shows the mold positioned on a femoral condyle.

DETAILED DESCRIPTION OF THE INVENTION

Figure 1A:
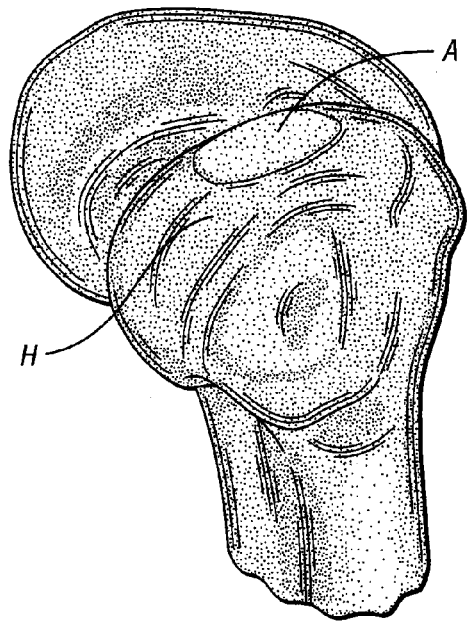
FIGS. 1a and 1b illustrate the destruction of articular material on the femoral condyle and tibial plateau, respectively.

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

The present invention includes a system and method for joint repair which reduce the amount of bone resection required for proper implant function. Since the amount of bone loss in the femoral condyle or tibial plateau is generally limited to a localized area of damage, only that area of bone loss is addressed. Rather than bring the surrounding healthy bone and cartilage down to the level of the defect (as is the typical method utilized in a TKR or UKR) and replace the resected material with a metal/polyethylene or all polyethylene plate, only the damaged area may be addressed with minimal or no loss of surrounding material. Furthermore, by replacing the original cartilage to its pre-diseased depth, the joint mechanical axis alignment may be restored to its original condition. In the knee, the system and method of the present invention can be used on both the tibial and femoral surfaces simultaneously, in either or both of the medial or lateral compartments, with or without the concurrent use of a spacer prosthesis.

In one embodiment, the system and method according to the present invention repair the joint surface by addressing only those particular areas of missing articular material and bone loss. As shown and described herein, the defects that result from osteoarthritis are typically localized such that the original shape of the femoral condyle and tibial plateau can be determined from the unaffected portions of the joint surfaces. In the case of more advanced disease, where osteophytes and bone loss are present, the rough shape of the femoral condyle and tibial plateau can still generally be restored to an approximation of their original shape.

While the system and method of the present invention are shown and described herein as being utilized in a knee joint, it is understood that the system and method could be utilized to reshape surfaces within any joint such as, but not limited to, the hip, shoulder, wrist, ankle, elbow, finger, and TMJ.

In one embodiment, the system and method of the present invention include placing an anatomically correct shaping member or mold 10 (for example, FIGS. 2a-2c) over a three-dimensional eburnated or diseased area A (see FIGS. 1a and 1b) of a mammalian joint surface in order to facilitate the repair of the diseased area through resurfacing while largely maintaining the integrity of the joint capsule. Once the mold 10 has been positioned, a repair material capable of replicating the volume and areal shape of the joint defect may be fashioned by depositing the repair material by any means under an inner surface 12 of the mold 10 and within the defect area A of the joint surface. This allows for either arthroscopic in situ joint repair of the surface, or ex vivo preparation of a custom implant. One surfacing mold 10 may typically be required for each degenerated surface restoration.

Figure 1B:
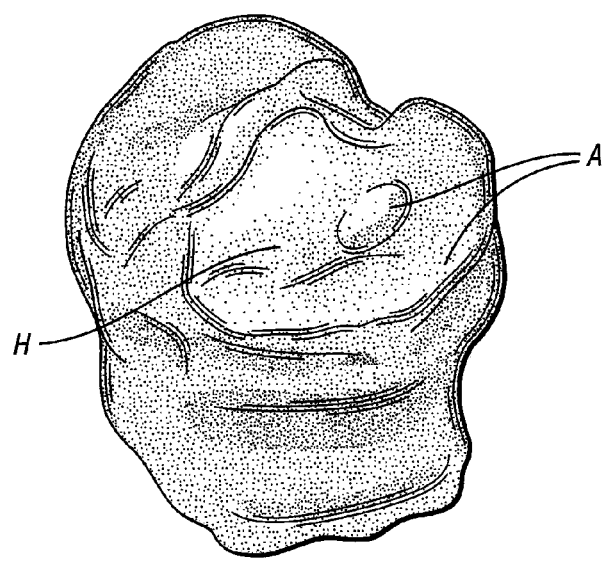
Figure 2A:
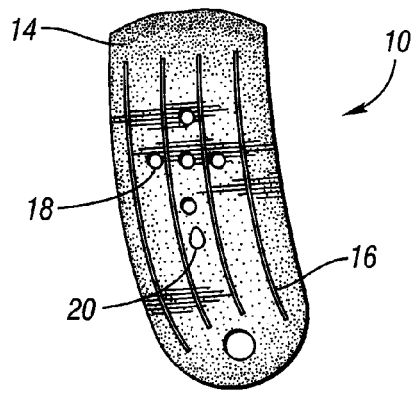
FIGS. 2a-2c are top plan, side elevational, and top perspective views, respectively, of a mold according to an aspect of the present invention.
Figure 2B:
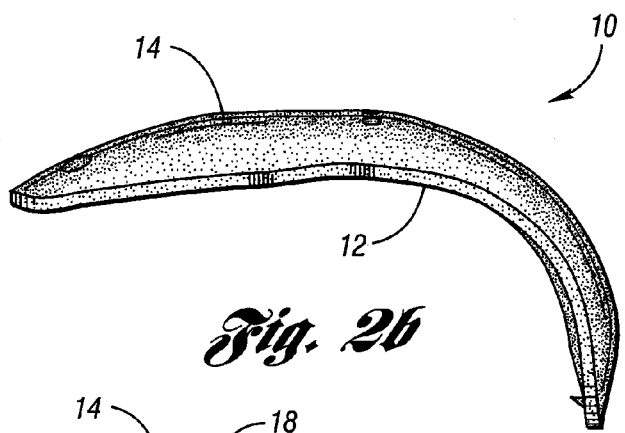
Figure 2C:
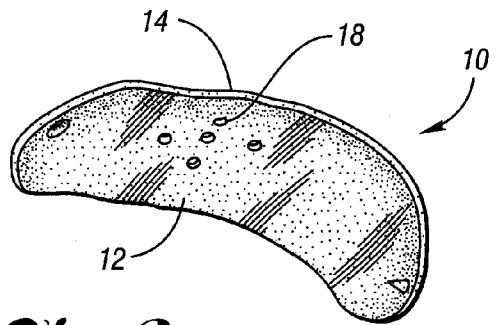

With reference to FIGS. 1a and 1b, the area A of degeneration is typically found in an area of the joint surface that once had a complex radius of smooth curvature and is now generally disfigured. The degenerated area is typically surrounded by ever increasing amounts of healthy joint cartilage H. According to one aspect of the present invention, the system and method described herein use the shape of the remaining healthy areas H to help form the mold 10 into a shape that resembles the surface of the joint prior to the degeneration.

In the case of the femoral condyle, typically, in either early or relatively advanced stages of osteoarthritis, the most anterior and posterior portions of the condyle remain in their original shape and geometry. Therefore, it is possible to span the defective area A with a semi-rigid mold 10 having an inner surface 12 and a outer surface 14 which can be shaped in an anterior-posterior direction as well as in a medial-lateral direction. Therefore, with such a mold 10 in place, the defect area A is completely covered by the mold 10, with the inner surface 12 of the mold 10 representing the original surface shape of the condyle before disease set in.

The actual shape of the mold 10 may be tailored to the individual. Generally speaking, each knee presents a different geometry of the respective femoral condyles and tibial plateaus. Even with respect to the right and left knees of a single individual, although bilateral symmetry dictates that the left and right knee components should be mirror images, this is often only an approximation. Thus, the shape of the affected femoral condyle and tibial plateau may be ascertained to determine the most appropriate mold 10 for a given patient.

Figure 3A:
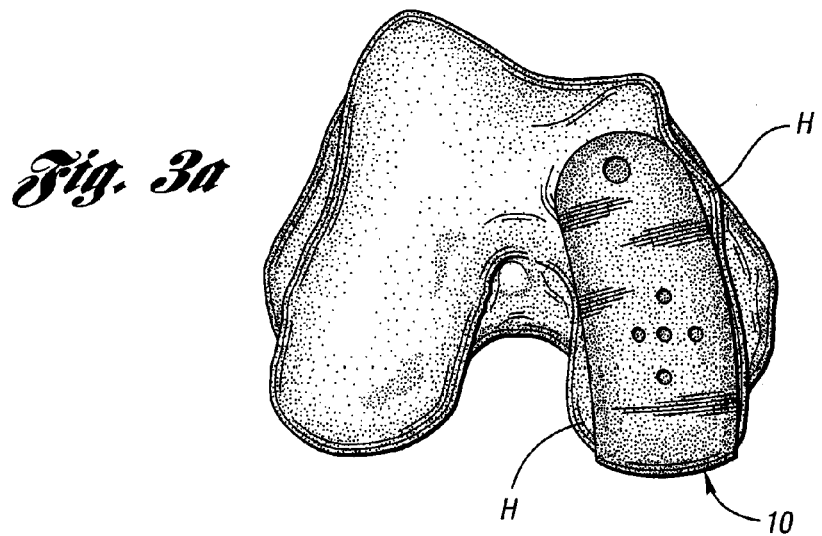
FIGS. 3a and 3b are top plan and side elevational views, respectively, of the mold of FIGS. 2a-2c positioned on a femoral condyle.
Figure 3B:
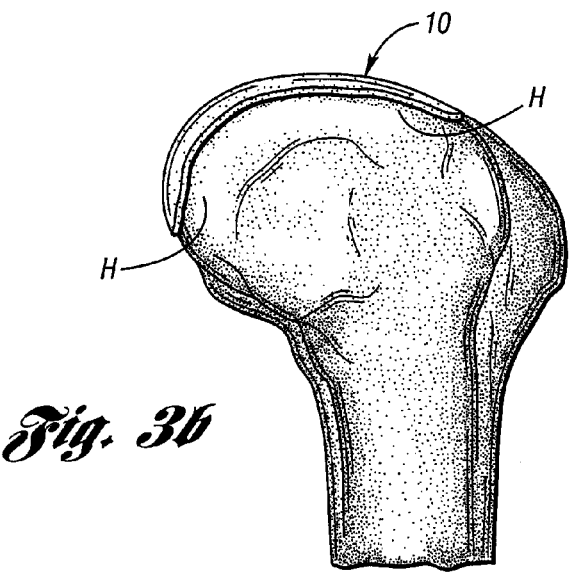

Mold 10 may comprise a relatively stiff material, wherein the mold shape is created for a particular patient by bending the mold 10 over the degenerated joint area A until the mold 10 contacts the surrounding healthy cartilage H (see FIGS. 3a and 3b). The stiffness of the mold material causes it to "bridge" the defective area A, leaving a gap between the mold 10 and the degenerated joint surface A. The mold 10 may be able to bend in both the length and width directions without wrinkling of the mold material. The shape of the mold 10 thus formed closely resembles the original joint surface.

The bending of the stiff mold material can be accomplished via several methods. For example, a longitudinally and transversely curved mold material may be attached to one of the anterior or posterior joint surfaces via temporary means (e.g., hooks, screws, etc.). By tensioning the mold 10 against the opposed healthy surface H, the mold material may generally conform to the pre-disease joint shape in both the longitudinal and transverse dimensions. The mold material can be predisposed to the cross-forming shape by including stiffening members 16 therein (see FIG. 2a) which may include multiple unidirectional (for example, in the longitudinal direction) elements joined with flexible material between each of the elements. Alternatively, the mold 10 can be made of materials of differing modulus, allowing for the formation of a complex shape without wrinkling of the face of the mold material.

According to another aspect of the present invention, a pre-formed mold that is custom-tailored to each individual could be utilized. To prepare such a mold, the patient's knee joint could be examined by a non-invasive imaging procedure (e.g., X-ray, MRI, or the like). A contour plot of the femoral and tibial mating joint surfaces and the size of the meniscal cavity can be generated from imaging data by a suitable computer program. From the contour plot, the correct surface geometry of the mold could be determined from the shape of the respective tibial plateau and femoral condyle, and the orientation between the two surfaces, such as in extension.

The mold 10 of the present invention may be applied within the joint using vacuum assistance, such as by application to bleed holes 18 (see FIG. 2a) which may be present in the mold 10, in order to assure a void-free filling of the defect area A. In one embodiment, the mold 10 may include a hard, yet somewhat deformable central shape which may be generically molded for a particular sized knee (for example, 38 to 62 mm AP radius). Beyond the center section may be sealable, more compliant edges for easy sealing to the adjacent structures. The mold 10 according to the present invention may also allow the surgeon to selectively cure the edges while leaving a center, weight-bearing area uncured for final shaping. The mold 10 may be constructed from any material suitable for the intended purpose. According to one aspect of the present invention, the mold 10 may be generally clear, transparent, or translucent, such as made from acrylic, polycarbonate, urethane, polyethylene or other suitably quasi-transparent material. This may facilitate the viewing of the injected repair material for purposes of void detection and final shaping. Further, use of translucent mold materials allows for the incorporation of an internal light diffuser 20 (see FIG. 2a), such as a prismatic light diffuser, which may allow a light source to enter the mold 10 from one point of entry and be re-emitted over the larger internal surface area of the mold 10.

With the mold 10 positioned in the joint (FIGS. 3a and 3b), a repair material 50 (best shown in FIGS. 4a and 4b), which may comprise a multi-stage, quasi-biologic or structural material, may be deposited using any injection device (for example, but not limited to, a syringe or the like) under the mold inner surface 12 and into the degenerated area A that was caused by the osteoarthritis, where the repair material 50 may be rigidized into a structural, load-bearing surface. The repair material 50 may include any material suitable for repair of the joint surface. In one example, the repair material 50 may include photoinitialized or photocured polymers which may or may not contain chondrocytes or precursor cells (MSCs) to articular cartilage which become fully characterized as to all of its components and have the ability to become a permanent or semi-permanent component of the joint surface. The repair material 50 may be two-stage in that a subsurface component may have more bone-like qualities and an outer component may be more articular-like in nature. Additionally, the repair material 50 may contain living cells, or may include a biologically or pharmaceutically active material such as, for example, one that promotes tissue regrowth, retards tissue degeneration, or decreases inflammation. Such active materials may be designed to be delivered at once or in a timed-release manner.

According to one non-limiting aspect of the present invention, the viscosity of the repair material 50 can be approximately 50,000 cps+/−20,000. This viscosity allows for less running out of the mold 10. The repair material 50 can be partially cured, or the cure may be initialized at the time of injection by adding a light source to the injection device, such as an arthroscopic light source.

Figure 4A:
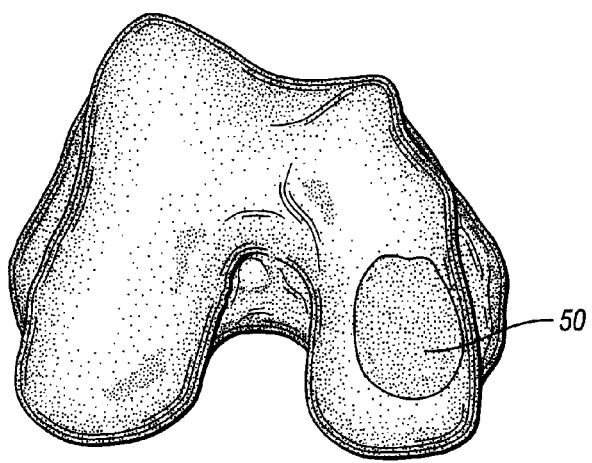
FIGS. 4a and 4b are top plan and top perspective views, respectively, of repair material deposited on the femoral condyle according to the present invention.
Figure 4B:
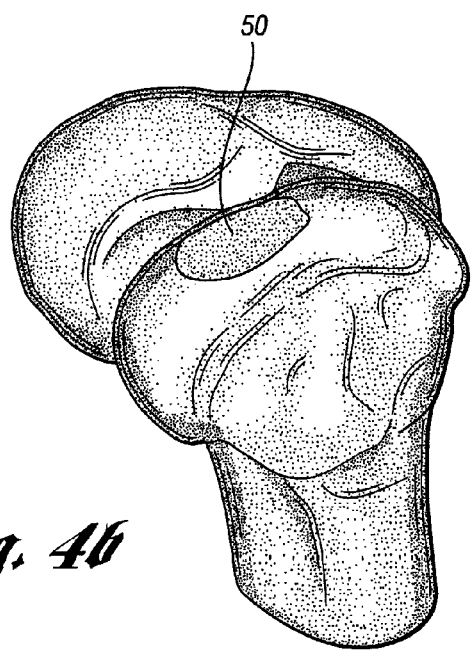

After curing of the repair material 50, the mold 10 may be removed from the joint, the edges of the deposited repair material 50 may be cleaned, and the joint surface will have been restored to very near its original shape. In this manner, the mold 10 according to the present invention acts as a temporary member for purposes of re-creating the original shape of the joint surface (FIGS. 4a and 4b). The molding system and method according to the present invention may allow for a smooth, anatomically (for the particular vs. generic patient) correct shape. The system and method described herein may also allow for a good "feather" into the surrounding healthy, yet thin-transitioning-to-full depth articular material which is typically found in these patients. The repair material 50 can be replaced by biologic material over time.

According to one aspect of the present invention, the method may include restoring a first joint surface, and then using that restored first joint surface to assist in forming the mold for restoring a second joint surface, which may be an opposing joint surface. When used in the knee, the surface of the femoral condyle may be restored first, and then the tibial plateau within the same compartment may be repaired. Of course, the system and method of the present invention is not limited to these repairs or order of repairs.

Figure 5A:
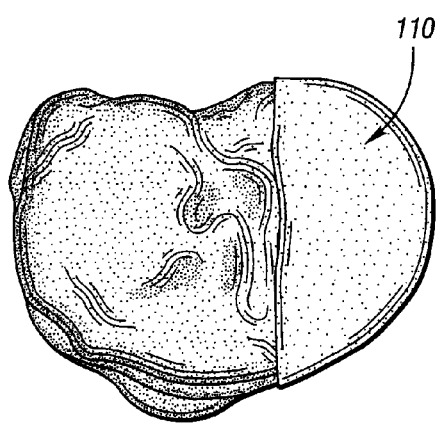
FIGS. 5a and 5b are top plan and top perspective views, respectively, of a mold according to another aspect of the present invention positioned on the tibial plateau.
Figure 5B:
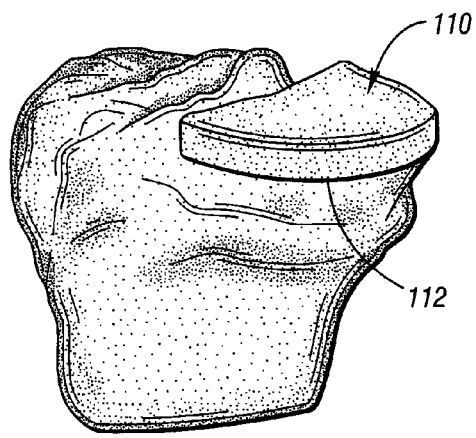

Turning to FIGS. 5a and 5b, with respect to the tibial plateau, the method according to the present invention can include placing a mold 110, which may be semi-rigid, on the joint surface and attaching the mold 110 via temporary means. The mold material can then be deformed by coming into contact with the just repaired opposite joint surface (i.e., the femoral condyle in this case) or the mold 10 for the opposite joint surface. This will result in a depression being formed in the mold 110, which will allow for the proper gap between the joint surfaces throughout the entire ROM.

In the case of the femoral and tibial surfaces, the difference in the tibial mold 110 compared with the femoral mold 10 is that the concave nature of the tibia (on the medial side) is a direct result of the femoral shape as well as the particular ligament structure present. Both of these factors will ultimately determine the knee's particular kinematic ROM. With the tibial mold 110 in place and the knee placed in full extension and distracted to the limits of the ligament structure, a concave shape may be created in the tibial mold 110 by the shape of the femoral condyle which has just previously been restored.

Figure 6A:
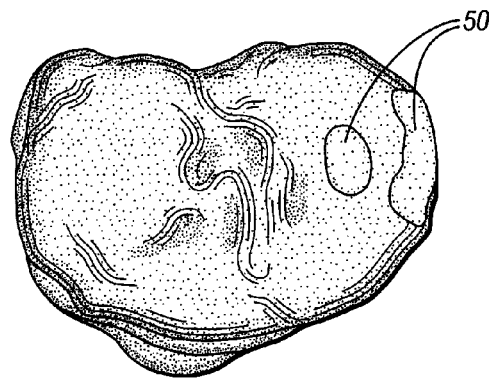
FIGS. 6a and 6b are top plan and top perspective views, respectively, of repair material deposited on the tibial plateau according to the present invention.
Figure 6B:
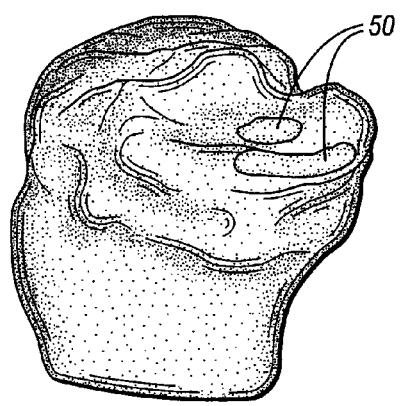

Once the tibial mold 110 is in place, the same repair material deposition may be performed as described above with reference to the femoral condyle, filling in only those areas that are not in intimate contact with the inner surface 112 of the tibial mold 110. After curing of the repair material 50, the tibial mold 110 may be removed, leaving a restored tibial surface (FIGS. 6a and 6b). The repair material 50 can be replaced by biologic material over time.

In restoring the femoral and tibial surfaces, the repair material 50 may be injected under pressure, such as either vacuum assisted or under pressurized assistance, via passage of the repair material 50 under the inner surface 12, 112 of the mold 10, 110, through the mold 10, 110 itself, via an endoscopic approach through the underlying, supporting bone structure, or by any other means.

At the conclusion of these procedures, the joint may be left in a close to original configuration as far as shape, ROM, and knee kinematics are concerned. Thus, the knee will have been restored via a procedure that, conceivably, can be repeated as often as necessary, or as necessary as repair materials may be improved over time. One potential advantage of the system and method of the present invention, in comparison with other approaches such as periosteum transplantations, is that the patient may be able to have a full weight-bearing post-operative experience and the surgical procedure itself should be significantly less demanding on the surgeon and much less traumatic for the patient.

Figure 7:
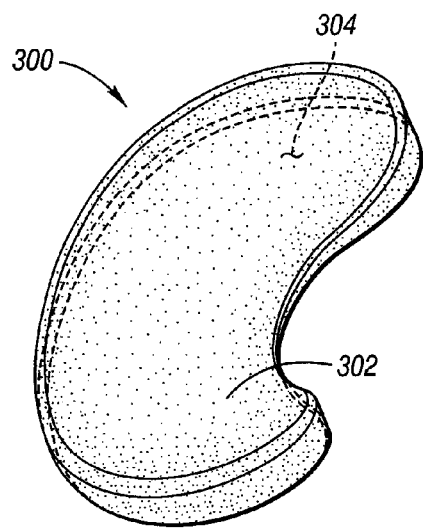
FIG. 7 illustrates a spacer prosthesis which may be utilized in accordance with the system and method of the present invention.

With reference to FIG. 7, a spacer prosthesis 300 can be used in conjunction with the system and method of the present invention to serve a mensical function, or also for purposes of protecting growing fibrocartilage. The surfaces formed for the femoral and tibial molds 10, 110 can be duplicated on the femoral 302 and tibial 304 surfaces of the spacer prosthesis 300 to create a conformal prosthesis, thus minimizing wear. The prosthesis 300 may be as described in U.S. Pat. Nos. 6,206,927 and 6,558,421 and copending U.S. application Ser. No. 10/232,608, each incorporated by reference herein.

In certain conventional methods, the surgeon prepares the femoral and tibial surfaces with specialized rasps and other tools. The mold material may be pre-formed, ex vivo, and then shaped in final form upon attachment to the tibia and with applied pressure from the femur. As such, the material may take on the shape of the femoral condyle as prepared by the surgeon, and not necessarily the original shape of the joint prior to disease and degeneration.

Thus, while conventional methods may employ a generic mold shape or utilize a mold shape defined by the surgeon, the system and method according to the present invention advantageously may utilize a mold shape that is determined by the patient's own prior anatomy. Furthermore, in comparison with prior art systems, the mold of the present invention may also be easier to apply and may not require a subsequent remodeling of the subchondral bone as the loads will be further distributed without disturbing the underlying structure.

The mold 10, 110 according to the present invention is based upon the shape of the surrounding healthy cartilage, and allows for filling of the defect area A using a patient-specific mold. In addition, the sequence according to one aspect of the present invention of first forming the femoral side, thus defining the shape of the femoral surface, and then using that shape as the limiting factor in the tibial shape/filling amount allows for a full restoration back to original joint shapes.

According to another aspect of the system and method of the present invention, the femoral and tibial molds 10, 110 can be made from extremely thin man-made materials that can be adjusted in place at the time of surgery. Their structural properties can be enhanced by back-filling the defect areas A with a structural reinforcing material, thus increasing the properties of the covering components.

Figure 8A:
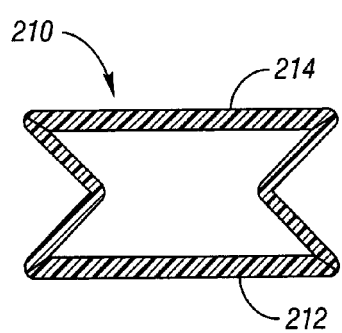
FIGS. 8a and 8b are schematic illustrations of a balloon mold according to the present invention in collapsed and expanded configurations, respectively.
Figure 8B:
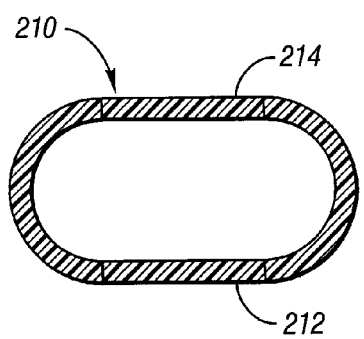
Figure 9A:
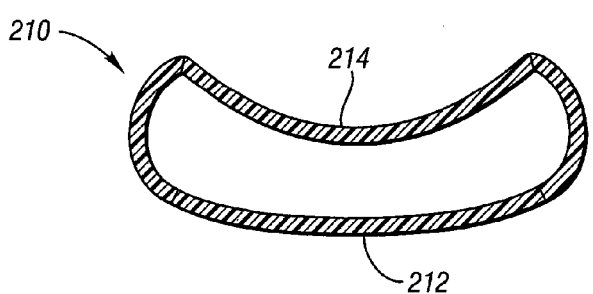
FIGS. 9a and 9b are schematic illustrations of exemplary molds which may be utilized for the knee joint in accordance with the present invention.
Figure 9B:
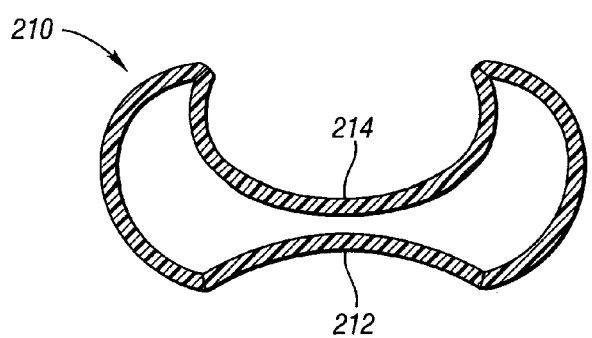
Figure 10:
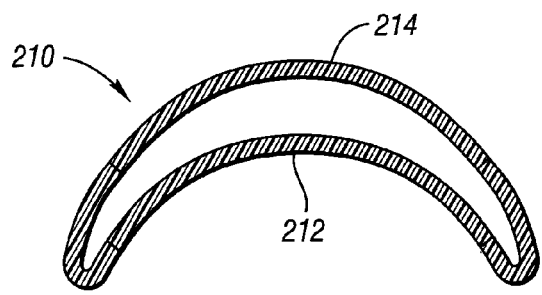
FIG. 10 is a schematic illustration of an exemplary mold suitable for shaping a hip, shoulder, or finger joint according to the present invention.

With reference to FIGS. 8a and 8b, a balloon type mold 210 can be provided with a generally rigid surface on one or both of its bottom 212 and top 214 surfaces. The balloon mold 210 may be capable of being collapsed as illustrated in FIG. 8a, such as in order to be inserted through an arthroscopic portal in the joint capsule, and then filled with gas or fluid and expanded as illustrated in FIG. 8b once inside the joint space. In one embodiment, the balloon mold 210 may include only one generally rigid surface designed for repair of one of the tibial or femoral surfaces. In another embodiment, the balloon mold 210 can include opposing generally rigid surfaces to allow simultaneous repair of both joint surfaces. With reference to FIGS. 9a and 9b, exemplary shapes of balloon molds 210 which may be suitable for repair of one or both of the femoral condyle and tibial plateau of the medial compartment and lateral compartment, respectively, are depicted, wherein FIG. 10 depicts an exemplary shape of a balloon mold 210 which may be suitable for repair of the hip, shoulder, and finger. In comparison with certain previous methods, embodiments of the system and method of the present invention advantageously form the repair material 50 against the joint surface directly, thus allowing for the direct bonding of the repair material 50 to the joint surface that is desired. Using the mold 210 of present invention to perform single side repairs allows the amount of gap after filling to be controlled.

Figure 11A:
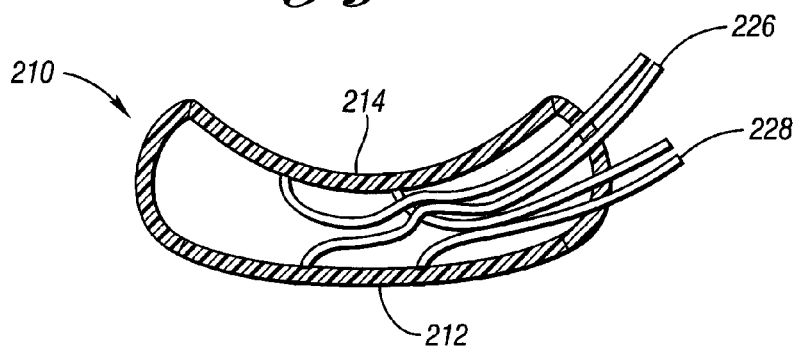
FIGS. 11a and 11b illustrate a balloon mold according to the present invention, where
Figure 11B:
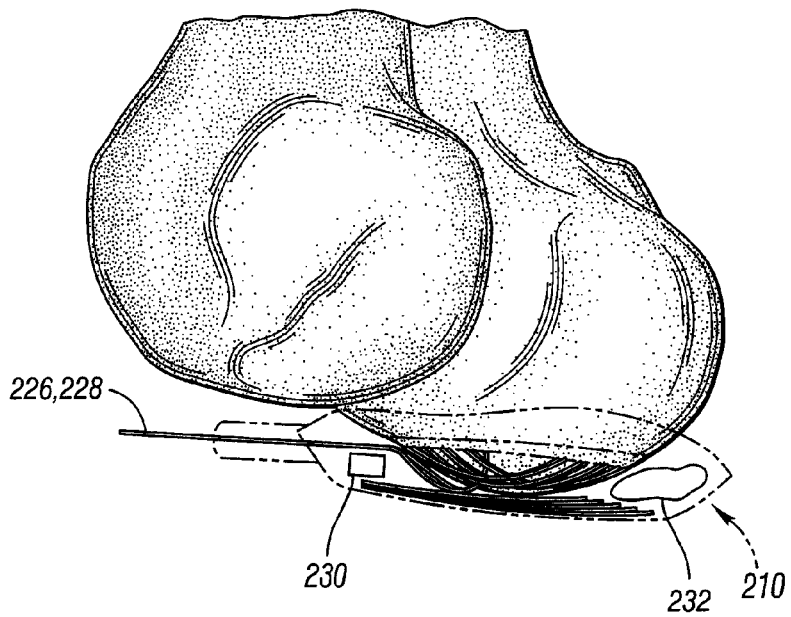

In a minimally invasive manner, the repair material 50 may be deposited under pressure, either vacuum assisted or under pressurized assistance, via passage of the repair material 50 under the bottom 212 or top 214 surfaces of the mold 210, through the mold 210 itself, via an endoscopic approach through the underlying, supporting bone structure, or any other means. With reference to FIGS. 11a and 11b, vacuum ports 226, fill ports 228, and associated internal tubing or passages may be incorporated in communication with one or both mold surfaces 212, 214 to allow for the evacuation of the area to be filled and filling of the defect area A with the repair material 50, respectively. Turning now to FIG. 11b, proper filling of the defect area A may be determined with internal sensors 230 that sense pressure, deformation of the mold 210, contact with the opposing joint surface, or the like. In addition to or in conjunction with the repair material 50, the balloon mold 210 according to the present invention could also include a reservoir 232 which may contain substances (for example, but not limited to, nutrients to enhance articular growth) to be released at once or in a timed-release manner. Such substances may be replenished from an outside source or as needed by direct injection.

It is understood that the features described above with reference to balloon mold 210 may also apply to mold 10 or mold 110, and vice versa.

According to any of the above aspects of the present invention, the mold material may be polymeric, ceramic, or metallic, but is not limited thereto. It can be pre-shaped to a generic sizing with the ability to be contoured to the final shape and dimensions by the surgeon. Thus, the material may have the ability to controllably deform to the desired shape via tensioning devices, via applied internal pressure, or via inherent shape memory properties. In one example, it can take the form of a laminate of such materials where the inner surface is a plastic film and the outer surface is a mesh with tensioning fibers that control the ML and AP shape.

In any of the approaches of the present invention, a pre-molded (ex vivo) or molded in place (in vivo), generic bone substitute may be used as the bulk of the repair material 50 with an overcoat of a bearing material, thus increasing the bearing strength of the repair as well as ensuring the proper density of the underlying support structure. Materials used as either the bone substitute or underlying structural materials may include, but are not limited to, polymeric, ceramic, or metallic materials. All may have the ability to mold quickly to the necessary shape or have the ability to be pre-molded. The outer layer of materials may possess the ability to crosslink or cure to a satisfactory degree of structural integrity within minutes of initialization by the surgeon. The outer layer may also possess qualities that allow it to translate and bear against itself (femoral condyle repair against tibial repair) without the formation of debris or permanent deformation of shape. Pre-molded shapes can be used with an "overcoat" of in vivo molded materials.

The above-described methods can be used to form in situ permanent repairs to the degenerated surfaces, or as a method to form a replica of the degenerated area to be used subsequently as a descriptor of the ultimate replacement material shape. Thus, one could form a "master" replica of the degenerated area, transfer those dimensions through some means of digital 3D volume conversion, and use that information to form a surface repair ex vivo for subsequent implementation.

An additional function of the molds according to the present invention can be realized in the following manner. In the case of a repair material that contains cellular materials such as chondrocytes, these materials may need to be in vivo for an extended length of time in order to maximize material properties and cellular growth. The mold, such as in the form of balloon mold 210, can be left in the joint to provide continual shaping pressures to the repair material while allowing the joint to have a limited to full range of motion. The mold 210 can be filled with any material suitable for providing the pressures required such as, but not limited to, air, saline, a temporary gel, a polymeric material, or an expanding foam.

An example of this would be to apply approximately a 2-15% deformation of the repaired area at a frequency of about 0.1-1 Hz with periods of rest if required. The inflation/deflation of the mold 210 can be cycled on-off for a prescribed period of time and frequency to assist in the growth and maturation of the repaired site. The mold 210 may be used in conjunction with a fixed covering material over the repair material to apply the continued pressure. A long-term use of mold 210 as described above allows for the use of a continuous passive motion (CPM) machine while maintaining pressure on the repaired site. Such a long-term mold 210 can act as a "removable" prosthesis where long term axis correction is not desired. In one embodiment, mold 210 may be made from a non-woven fabric made of resorbable material (such as, but not limited to, VICRYL®) and may be designed to deposit or leach materials over time to the affected areas while maintaining shape, pressure, and/or joint axis correction.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for repairing a defect area in a surface of a knee joint, the method comprising:
   providing a mold having a first surface and a second surface;
   positioning the mold within the knee joint such that a perimeter of the mold surrounds the defect area and the mold completely covers the defect area; and
   with the mold perimeter surrounding the defect area and the mold completely covering the defect area, injecting a repair material from under the mold first surface and within the defect area to create a repaired site within the knee joint.

2. The method according to claim 1, further comprising shaping the mold by contacting a healthy area of the joint surface with at least part of the mold first surface.

3. The method according to claim 1, wherein positioning the mold includes removably attaching the mold to a healthy area of the joint surface.

4. The method according to claim 1, further comprising evacuating the joint via a vacuum port in communication with at least one of the first and second mold surfaces.

5. The method according to claim 1, further comprising sensing filling of the defect area with the repair material via a sensor provided in the mold.

6. The method according to claim 1, further comprising releasing substances into the joint from a reservoir within the mold.

7. The method according to claim 1, wherein injecting the repair material includes injecting the repair material under pressure.

8. The method according to claim 1, wherein injecting the repair material includes introducing the repair material through an underlying bone structure into the defect area.

9. The method according to claim 1, further comprising restoring a first joint surface within the joint, and then using that restored first joint surface to assist in shaping a mold for restoring a second joint surface within the joint.

10. The method according to claim 1, wherein one of the first and second mold surfaces is arranged to contact a first joint surface, and the other of the first and second mold surfaces is arranged to contact a second, opposed joint surface.

11. The method according to claim 1, further comprising removing the mold from the joint.

12. The method according to claim 1, further comprising leaving the mold within the joint to provide shaping pressures to the repaired site.

13. The method according to claim 1, further comprising inserting a spacer prosthesis into the joint.

14. The method according to claim 1, further comprising examining the joint using a non-invasive imaging procedure to determine a shape of the mold.

15. A method for repairing a defect area in a surface of a knee joint, the method comprising:
   providing a mold having a first surface and a second surface;
   positioning the mold within the knee joint such that a perimeter of the mold surrounds the defect area;
   with the mold perimeter surrounding the defect area, injecting a repair material between the mold first surface and the defect area to create a repaired site within the knee joint; and
   sensing filling of the defect area with the repair material via a sensor provided in the mold.

16. A method for repairing defect areas in a first joint surface and a second joint surface of a knee joint, the method comprising:
   providing a mold having an inner surface and an outer surface;
   positioning the mold within the knee joint such that a perimeter of the mold surrounds a defect area in the first joint surface;
   with the mold perimeter surrounding the defect area, injecting a repair material between the mold inner surface and the defect area to create a restored first joint surface; and
   using the restored first joint surface to assist in shaping a mold for repairing a defect area in the second joint surface.

* * * * *